US008003831B1

(12) United States Patent
Ritter

(10) Patent No.: US 8,003,831 B1
(45) Date of Patent: Aug. 23, 2011

(54) PROCESS FOR THE SYNTHESIS OF DIHALODINITROBENZENES

(75) Inventor: Joachim C. Ritter, Wilmington, DE (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 163 days.

(21) Appl. No.: 12/335,959

(22) Filed: Dec. 16, 2008

Related U.S. Application Data

(60) Provisional application No. 61/014,515, filed on Dec. 18, 2007.

(51) Int. Cl.
C07C 205/00 (2006.01)
(52) U.S. Cl. .................................... 568/933
(58) Field of Classification Search .............. 568/933
See application file for complete search history.

(56) References Cited

U.S. PATENT DOCUMENTS

| 3,174,947 | A | 3/1965 | Marvel |
| 3,783,137 | A | 1/1974 | Gerber |
| 4,522,745 | A | 6/1985 | Kurkov |
| 4,533,692 | A | 8/1985 | Wolfe |
| 4,566,876 | A | 1/1986 | Brown et al. |
| 5,041,522 | A | 8/1991 | Dang |
| 5,574,188 | A | 11/1996 | Behre et al. |
| 5,674,969 | A | 10/1997 | Sikkema |
| 6,040,478 | A | 3/2000 | Sikkema |
| 6,093,852 | A | 7/2000 | Behre et al. |
| 2006/0287475 | A1 | 12/2006 | Allen |

FOREIGN PATENT DOCUMENTS

| JP | 01238561 | 9/1989 |
| JP | 07048321 | 2/1995 |
| JP | HEI 7 1995-48321 | 2/1995 |
| WO | 9425506 A1 | 11/1994 |

OTHER PUBLICATIONS

Suzuki et al (JP 07048321 computer translation to English) 1995.*
R. Nietzki et al., Synthese Von Symmetrischem Tetramidobenzol Mittels Dinitrodichlorbenzol., 1897, vol. 30:1666-1669.
Wolfgang Knobloch et al., Synthese Von 2.6-Disubstituierten Benzo [1.2.4.5] Bismidazolen, 1958, vol. 91:2562-2566.
J. H. Boyer et al., The Preparation of 6,7-Disubstituted Quinoxalines, Jacs, 1960, vol. 82:2213-2215.

* cited by examiner

Primary Examiner — Jafar Parsa

(57) ABSTRACT

A process is provided for the preparation of 1,3-dihalo-4,6-dinitrobenzene by the nitration of 1,3-dihalobenzene. The direct isolation of highly pure 1,3-dihalo-4,6-dinitrobenzene is accomplished without a water or ice quench, and involves the use of at least one equivalent of $SO_3$ during the reaction, slow crystallization, and isolation of product from a cold crystal slurry.

14 Claims, No Drawings

PROCESS FOR THE SYNTHESIS OF DIHALODINITROBENZENES

This application claims priority under 35 U.S.C. §119(e) from, and claims the benefit of, U.S. Provisional Application No. 61/014,515, filed Dec. 18, 2007, which is by this reference incorporated in its entirety as a part hereof for all purposes.

TECHNICAL FIELD

This disclosure relates to a process for the synthesis of 1,3-dihalo-4,6-dinitrobenzene.

BACKGROUND

The compound 1,3-dihalo-4,6-dinitrobenzene ("DHDNB"), which is represented by the structure of the following Formula (I),

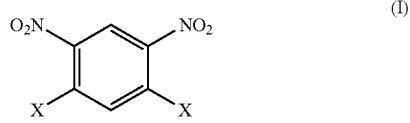

wherein each X is independently Br or Cl, is conventionally used as a starting material or intermediate in the preparation of a variety of products that include dyes, pharmaceuticals, pesticides, agrochemicals, and monomers for incorporation into polymers such as those described in WO 94/25506.

Known processes for the preparation, for example, of 1,3-dichloro-4,6-dinitrobenzene ("DCDNB") by the nitration of 1,3-dichlorobenzene, which is represented by the structure of the following Formula (II)

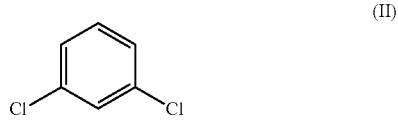

require a costly work-up procedure ("quench") wherein the product and sulfuric acid reaction mixture is added to a large quantity of ice and/or diluted with 5-10 times the volume of water. The large volumes, the difficulty of managing the exotherm associated with this quench procedure, and the difficulty of recycling the sulfuric acid result in considerable fixed and variable cost. It would thus be desirable to be able to eliminate the need for such a quench procedure.

For this reason, and because of a particular need for a process to make DCDNB with improved selectivity and high purity, a need remains for improved processes generally to make the various compounds of Formula (I).

SUMMARY

The inventions disclosed herein include processes for the preparation of a 1,3-dihalo-4,6-dinitrobenzene, processes for the preparation of products into which a 1,3-dihalo-4,6-dinitrobenzene can be converted, the use of such processes, and the products obtained and obtainable by such processes.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

One embodiment of this invention provides a process for preparing a 1,3-dihalo-4,6-dinitrobenzene by (a) admixing a 1,3-dihalobenzene, which is represented by the structure of the following Formula (III):

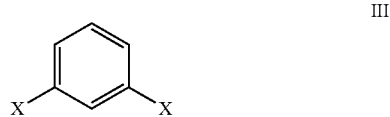

wherein each X is independently Cl or Br, with fuming nitric acid, sulfuric acid, and $SO_3$; to form a reaction mixture that is characterized by (i) a concentration of nitric acid therein that is in the range of about 2.0 to about 2.3 moles per mole of 1,3-dihalobenzene; (ii) a concentration of $SO_3$ therein that is in the range of about 1 to about 3 moles per mole of 1,3-dihalobenzene; (iii) a concentration of 1,3-dihalobenzene therein that is in the range of about 12 to about 24 weight percent; and (iv) a temperature of up to about 120° C.; and (b) stirring the reaction mixture at a temperature in the range of about −10° C. to about 70° C. to form a 1,3-dihalo-4,6-dinitrobenzene product.

One advantageous effect of isolating the crystalline product directly from the reaction mixture, without water quenching and subsequent crystallization steps, is that a high purity product is obtained.

DETAILED DESCRIPTION

One embodiment of this invention provides a process for preparing a 1,3-dihalo-4,6-dinitrobenzene by (a) admixing a 1,3-dihalobenzene, which is represented by the structure of the following Formula (III):

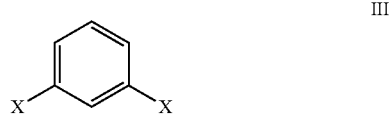

wherein each X is independently Cl or Br, with fuming nitric acid, sulfuric acid, and $SO_3$; to form a reaction mixture that is characterized by (i) a concentration of nitric acid therein that is in the range of about 2.0 to about 2.3 moles per mole of 1,3-dihalobenzene; (ii) a concentration of $SO_3$ therein that is in the range of about 1 to about 3 moles per mole of 1,3-dihalobenzene; (iii) a concentration of 1,3-dihalobenzene therein that is in the range of about 12 to about 24 weight percent; and (iv) a temperature of up to about 120° C.; and (b) stirring the reaction mixture at a temperature in the range of about −10° C. to about 70° C. to form a 1,3-dihalo-4,6-dinitrobenzene product.

In another embodiment, the process further comprises isolating the product 1,3-dihalo-4,6-dinitrobenzene from the reaction mixture by filtration, leaving a filtrate, wherein the filtrate comprises sulfuric acid and unrecovered product; extracting the unrecovered product from the filtrate, leaving an extracted filtrate comprising sulfuric acid; and recycling the extracted filtrate for use in the production of additional 1,3-dihalo-4,6-dinitrobenzene.

The concentration of nitric acid in the reaction mixture is in the range of about 2.0 to about 2.3 moles per mole of 1,3-dihalobenzoene ("mDHB"). Concentrated nitric acid (e.g. a commonly used reagent grade, which is about 70% nitric acid in water) can be used, but fuming nitric acid is preferred. The term "fuming nitric acid" denotes concentrated nitric acid containing dissolved nitrogen dioxide.

The concentration of $SO_3$ in the reaction mixture is in the range of about 1 to about 3 moles, preferably about 1.5 to about 2.25 moles, per mole of mDHB. $SO_3$ may be added to the reaction itself, or may be provided in the form of oleum (i.e. fuming sulfuric acid), which is anhydrous and is formed by dissolving excess sulfur trioxide ($SO_3$) into sulfuric acid. If concentrated nitric acid is used, sufficient $SO_3$ would be added to the reaction mixture to both remove water from the nitric acid (by reaction with it to form sulfuric acid) and to carry out the nitration reaction.

It is preferred, in the process hereof, to keep water at a level below one equivalent to increase the purity of the product. This can be achieved by adding at least 1 mol equivalent of a suitable water removing agent. The most suitable water removing agent in this case is $SO_3$. Preferably, 1.5-2.25 mol equivalents of $SO_3$ are introduced as described above to achieve the isolation of high purity 1,3-dihalo-4,6-dinitrobenzene. Under these circumstances, essentially all impurities, including the undesired isomer 1,3-dihalo-2,4-dinitrobenzene, remain in solution; and crystalline 1,3-dihalo-4,6-dinitrobenzene may typically be isolated in purity grades >99% at high yields.

The concentration of sulfuric acid in the reaction mixture is an amount such that the weight percent of mDHB therein (i.e. the weight of mDHB relative to the combined weight of mDHB plus the other components in the reaction mixture) is in the range of about 12 to about 24 weight percent.

1,3-dibromobenzene, 1,3-dichlorobenzene and 1-bromo-3-chlorobenzene are commercially available, for example, from Sigma-Aldrich (St. Louis Mo.)

The sulfuric acid, oleum/$SO_3$, and nitric acid may be combined with the mDHB in any possible addition mode, excluding those in which the mDHB is premixed with nitric acid or with oleum/$SO_3$ before adding it to the reaction vessel, and those in which mDHB and oleum/$SO_3$ are combined in the reaction vessel before nitric acid is added. Premixing the mDHB with nitric acid would cause an undesirable reaction. Contacting mDHB with oleum/$SO_3$ in the absence of nitric acid would cause undesirable sulfonic acids to form irreversibly.

Examples of possible modes of reactant addition to form the reaction mixture include without limitation adding mDHB to a mixture of nitric acid and sulfuric acid containing between 1 and 3 mol equivalents of $SO_3$ per mol equivalent of mDHB;

adding a mixture of oleum and nitric acid to a mixture of mDHB and an optional amount of sulfuric acid;

adding mDHB and oleum separately but concurrently to nitric acid; and adding mDHB and a mixture of oleum and nitric acid separately but concurrently to sulfuric acid.

During the addition of the reactants in the form of solution components, the temperature of the reaction mixture is maintained below 120° C., preferably below 60° C., and most preferably in the range of about −10° C. to about +15° C. by controlling the rate at which the components are added. The rate at which the mDHB is added will depend, for example, on the reaction temperature, the efficiency with which the reaction vessel can be cooled, and the batch size. In adjusting the time of addition of the reactants, the cooling capacity and heat transfer coefficient of the equipment used is readily determined using standard calorimetric and engineering methodology. Typical addition times may be about 30 minutes to several hours.

During the reaction, the temperature is maintained in the range of about −10° C. to about 40° C., preferably between about 0° C. and about 25° C. while the reaction mixture is stirred for an additional time period, typically a few hours, until the reaction is completed and no more heat of reaction is generated. Slow crystallization occurs as the DHDNB is precipitated. The slow crystallization results in a high-purity product.

In an optional step, better product yield may be obtained by increasing the temperature of the reaction following the completion of addition of all components rather than just stirring the reaction mixture as this will convert small amounts of starting materials and intermediates to product. This step is intended to shorten the time to reaction completion by removing trace amounts of intermediates. In this optional step, it is preferred that the temperature of the reaction mixture not exceed a temperature of 120° C., and more preferred that it not exceed 85° C. Heating rates will depend, for example, on the efficiency with which the reaction vessel can be heated and the batch size. Typical heating times may be about 30 minutes to several hours. The reaction is allowed to occur at the elevated temperature for a short time, typically about 10 minutes to about an hour. The reaction mixture is then cooled, or is permitted to cool, to a temperature in the range of about 30° C. to about 70° C. to allow slow crystallization as the DHDNB product is precipitated. The slow crystallization assists in the formation of a high-purity product.

The product can then be isolated from the reaction mixture, which is preferably in the form of a cold crystal slurry. The preferred isolation temperature for the 1,3-dihalo-4,6-dinitrobenzene product depends on its concentration and on the amount of impurities present, but is generally chosen between about 0° C. and about 40° C. For a 1,3-dihalo-4,6-dinitrobenzene concentration of up to about 20% by weight, the preferred isolation temperature is between about 0° C. and about 10° C.

Controlling the feed rate and the reaction temperature promotes increased selectivity, which is often greater than 91% for 1,3-dichloro-4,6-dinitrobenzene specifically. The direct isolation of highly pure 1,3-dihalo-4,6-dinitrobenzene may thus be accomplished without a water or ice quench, by providing at least one equivalent of $SO_3$ during the reaction, slow crystallization, and isolation of product from a cold crystal slurry. This allows for the isolation of high-purity product.

As a result, the process hereof produces 1,3-dichloro-4,6-dinitrobenzene of 99.8% purity at a typical net yield of 80%. The term "purity" denotes what percentage of an in-hand, isolated sample is actually the specified substance. The term "net yield" of product denotes the actual, in-hand yield, i.e. the theoretical maximum yield minus losses incurred in the course of activities such as isolating, handling, drying, and the like.

In another embodiment, the process further comprises isolating the product 1,3-dihalo-4,6-dinitrobenzene from the reaction mixture by filtration, leaving a filtrate that contains sulfuric acid and unrecovered product; extracting the unrecovered product from the filtrate, leaving an extracted filtrate that contains sulfuric acid; and recycling the extracted filtrate (the "sulfuric acid mother liquor") to the reaction mixture for use in the production of more 1,3-dihalo-4,6-dinitrobenzene. An arrangement of this type is shown schematically as follows:

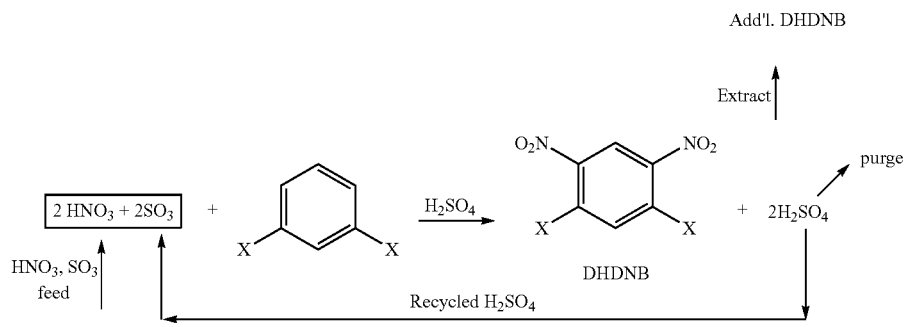

The unrecovered DHDNB is recovered by extracting the $H_2SO_4$ with a solvent such as toluene. Such extraction is carried out at about room temperature to avoid reaction. The DHDNB obtained by extraction is precipitated and the toluene or other solvent is reused. The extracted sulfuric acid mother liquor is directly recycled without water quench. Because $H_2SO_4$ is continually produced, a purge (e.g. about 10 vol %) is withdrawn as shown.

In a process hereof, the product and sulfuric acid reaction mixture is not added to a large quantity of ice, nor diluted with 5-10 times the volume of water. As a consequence, the process is conducted in the absence of an ice or water quench, and the volume of recyclable sulfuric acid mother liquor generated is much lower than in previous processes.

In a process hereof, highly pure product is produced at high selectivity and net yield. The large volumes, the difficulty of managing the exotherm associated with a water or ice quench procedure, and the difficulty for recycling the sulfuric acid characteristic of previous processes are avoided in the process described herein, resulting in considerable fixed and variable cost savings.

EXAMPLES

The advantageous attributes and effects of the processes hereof may be seen in a series of examples as described below. The embodiments of these processes on which the examples are based are representative only, and the selection of those embodiments to illustrate the invention does not indicate that materials, reactants, conditions, steps, techniques, or protocols not described in these examples are not suitable for practicing these processes, or that subject matter not described in these examples is excluded from the scope of the appended claims and equivalents thereof.

In the examples, the meaning of certain abbreviations is as follows: "d" means density, "equiv" means equivalent(s), "g" means gram(s), "GC" means gas chromatography, "$^1$H-NMR" means proton nuclear magnetic resonance spectroscopy, "h" means hour(s), "L" means liter(s), "mL" means milliliter(s), "min" means minutes, and "mol" means mole(s).

Example 1

To a 1 L 3-neck round bottom flask equipped with external ice cooling, mechanical stirrer, addition funnel, $N_2$ inlet, and thermometer was added 126 g (2 mol) fuming nitric acid (d=1.54), followed by 208 g sulfuric acid and 508 g 30% oleum (2.2 molar equiv $SO_3$) maintaining a temperature between 10° C. and 40° C. Subsequently, 140 g (0.95 mol) 1,3-dichlorobenzene (Toray Ltd., Tokyo JP, >99% purity) were added over a time period of 90 min while maintaining a temperature of about 5° C. The ice bath was removed, and the reaction mixture was allowed to warm up to room temperature. It was then heated from room temperature to 100° C. over a time period of 45 min. At that point, a small sample of crude product was taken from the reaction vessel and poured into ice water. The crude product was extracted with methylene chloride. Analysis by GC and $^1$H-NMR indicated a reaction selectivity to 1,3-dichloro-4,6-dinitrobenzene of 92%. After 15 min at 100° C., the reaction mixture was allowed to cool to room temperature over 2 h and then cooled to 5° C. over 30 min, after which it was filtered through a glass fritted funnel and washed with 300 mL water followed by 200 mL 10% aqueous $NH_3$ solution. After drying, 179 g of >99% pure product were isolated (80% net yield).

Example 2

This example was carried out as described in Example 1 but with half the amount of 30% $SO_3$ added. The net yield was 82%, and the purity was 96%

Example 3

This example was carried out as described in Example 1 but on a larger scale, using 1000 g 1,3-dichlorobenzene, 921.1 g fuming nitric acid (d=1.54), 3625.0 g oleum (30%) and 1485.7 g sulfuric acid in a 5 L glass reactor. The net yield was 83% and the purity was 99%.

Control A

This run was carried out as described in Example 1, but the reaction temperature was kept between 30 and 90° C. and the traditional workup procedure (here, an ice quench) was used. Sampling the reaction mixture before the work up procedure indicated a reaction selectivity of about 83%. The reaction mixture poured onto 750 g of ice (quenched), and the crude product was isolated by filtration. The net yield of 1,3-dichloro-4,6-dinitrobenzene was 73% with a purity of 84%. The main impurity was 1,3-dichloro-2,4-dinitrobenzene. Recrystallization of the crude product from a saturated solution in ethanol improved purity to 98-99%, but the net yield was only 60%.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

What is claimed is:

1. A process for preparing a 1,3-dihalo-4,6-dinitrobenzene comprising:
   (a) admixing a 1,3-dihalobenzene, which is represented by the structure of the following Formula (III):

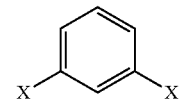

III wherein each X is independently Cl or Br, with fuming nitric acid having a density of 1.54, sulfuric acid, and $SO_3$ to form a reaction mixture that is characterized by (i) a concentration of nitric acid therein that is in the range of about 2.0 to about 2.3 moles per mole of 1,3-dihalobenzene; (ii) a concentration of $SO_3$ therein that is in the range of about 1 to about 3 moles per mole of 1,3-dihalobenzene; (iii) a concentration of 1,3-dihalobenzene therein that is in the range of about 12 to about 24 weight percent; and (iv) a temperature of up to about 10° C. to about 40° C.; and
   (b) stirring the reaction mixture at a temperature of about 100° C. to about 120° C. for at least about 15 minutes to form a 1,3-dihalo-4,6-dinitrobenzene product, and
   (c) cooling the reaction to a temperature at which the 1,3-dihalo-4,6-dinitrobenzene product crystallizes.

2. A process according to claim 1 further comprising permitting the reaction mixture to cool to room temperature prior to step (c).

3. A process according to claim 1 further comprising a step of isolating a 1,3-dihalo-4,6-dinitrobenzene product from the reaction mixture at a temperature between about 0° C. and about 40° C.

4. A process according to claim 1 wherein the concentration of $SO_3$ is in the range of about 1.5 to about 2 moles per mole of 1,3-dihalobenzene.

5. A process according to claim 1 wherein the temperature of the reaction mixture in step (a) is in the range of about −10° C. to about +15° C.

6. A process according to claim 1 wherein the concentration of 1,3-dihalo-4,6-dinitrobenzene product in the reaction mixture in step (b) does not exceed about 20% by weight, and the 1,3-dihalo-4,6-dinitrobenzene product is isolated from the reaction mixture at a temperature in the range of about 0° C. to about 10° C.

7. A process according to claim 1 wherein $SO_3$ is provided to the reaction mixture in the form of oleum, and wherein
   (e) 1,3-dihalobenzene is added to a mixture of fuming nitric acid, oleum, and sulfuric acid;
   (f) a mixture of oleum and fuming nitric acid is added to a mixture of 1,3-dihalobenzene and sulfuric acid;
   (g) 1,3-dihalobenzene and oleum are added separately but concurrently to fuming nitric acid; or
   (h) 1,3-dihalobenzene and a mixture of oleum and fuming nitric acid are added separately but concurrently to sulfuric acid;
   to form the reaction mixture.

8. A process according to claim 1 further comprising filtering the reaction mixture to isolate a 1,3-dihalo-4,6-dinitrobenzene product, leaving a filtrate that comprises sulfuric acid and unrecovered product.

9. A process according to claim 8 further comprising a step of extracting unrecovered product from the filtrate, leaving an extracted filtrate comprising sulfuric acid.

10. A process according to claim 9 further comprising a step of recycling the extracted filtrate to the reaction mixture for the preparation of additional 1,3-dihalo-4,6-dinitrobenzene product.

11. A process according to claim 1 wherein the reaction is run for a time period in the range of about 10 min to about 1 hour.

12. A process according to claim 1 wherein $SO_3$ is provided to the reaction mixture in the form of oleum.

13. A process according to claim 1 wherein the 1,3-dihalo-4,6-dinitrobenzene produced is at least of 96% purity.

14. A process according to claim 1 wherein the reaction mixture is incubated at 100° C. to about 120° C. for 15 minutes.

* * * * *